United States Patent [19]

Ohtsubo et al.

[11] Patent Number: 4,939,269

[45] Date of Patent: Jul. 3, 1990

[54] 3-SUBSTITUTED HYDANTOINS

[75] Inventors: Akihiro Ohtsubo; Kouhei Morikawa, both of Kawasaki; Yohko Kataoka; Sumio Soya, both of Yokohama, all of Japan

[73] Assignee: Showa Denko K. K., Tokyo, Japan

[21] Appl. No.: 285,632

[22] Filed: Dec. 16, 1988

[51] Int. Cl.[5] ........................................... C07D 233/74

[52] U.S. Cl. ................................................... 548/308

[58] Field of Search ........................................ 548/308

[56] References Cited

U.S. PATENT DOCUMENTS 4,203,619 5/1980 Sanders et al. ................. 428/914 X

FOREIGN PATENT DOCUMENTS 2092767 8/1982 United Kingdom .

OTHER PUBLICATIONS

*Chemical Abstracts,* 62:16258c (1965) [France 1,389,841, 2/19/65].

Findbeiner, H., *J. Org. Chem.,* 30, 3414–3419 (1965).

*Primary Examiner*—Richard A. Schwartz
*Attorney, Agent, or Firm*—Oblon, Spivak, McClelland, Maier & Neustadt

[57] ABSTRACT

A hydantoin compound of the formula:

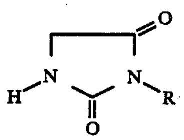

(wherein R stands for an alkyl group of 8 to 20 carbon atoms) increases the sensitivity of a color developing reaction of a heat-sensitive recording material and enhances the high-speed recording property of The recordig matvrial Without sacifice of the whiteness thereof. The heat-sensitive recording material containing the hydantoin compound is novel to the art.

1 Claim, No Drawings

3-SUBSTITUTED HYDANTOINS

BACKGROUND OF THE INVENTION

1. Field of the Invention

This invention relates to an additive for a heat-sensitive recording material, more specifically an additive for use (in a heat-sensitive recording layer of a heat-sensitive recording material) utilizing the reaction of a colorless or slightly colored basic dye with a (developer capable of producing a color on contact with the dye) to a heat-sensitive recording material containing the additive, and to a method for the production of the heat-sensitive recording material.

2. Prior Art Statement

The heat-sensitive recording material which comprises a sheetlike substrate (such as paper or polyester sheet), a heat-sensitive recording layer superposed on the substrate and composed of a basic dye and a developer capable of reacting with and coloring the dye on exposure to heat, and optionally a surface-protecting layer formed on the heat-sensitive recording layer has been finding extensive utility in various heat-sensitive recording devices such as heat-sensitive facsimile systems, heat-sensitive printer, etc. Recent years have seen rapid improvement, diversification, and performance enhancement of heat-sensitive recording devices. As a result, increasing demand has arisen for higher quality heat-sensitive recording materials, particularly for materials with high sensitivity usable for high-speed recording.

Numerous proposals have been made as to the combined use of heat-fusible substances (such as fatty acid amides, oils, and fats) as an additive aimed at enhancing the sensitivity of heat-sensitive recording materials. However the enhancement of recording sensitivity entails new drawbacks such as lower stability of the heat-sensitive recording layer, degradation of whiteness of the recording layer, and none of the heat-fusible substances proposed to date for the combined use has enabled production of a satisfactory heat-sensitive recording material.

OBJECT AND SUMMARY OF THE INVENTION

An object of this invention is to provide a novel additive for use in the heat-sensitive recording layer of a heat-sensitive recording material utilizing the reaction of a basic dye with a developer.

Another object of this invention is to provide an additive having the ability to enhance the sensitivity of the reaction of the basic dye with the developer when the heat-sensitive recording layer is melted by heat.

A further object of this invention is to provide an additive for the heat-sensitive recording material, which additive improves the high-speed recording property of the heat-sensitive recording material without sacrificing the whiteness of the recording layer.

Yet another object of this invention is to provide a heat-sensitive recording material containing the additive mentioned above. Still another object of this invention is to provide a method for the production of the heat-sensitive recording material containing the aforementioned additive.

The inventors continued a study on a wide variety of compounds in search of a highly satisfactory additive useful for the ideal heat-sensitive recording material aimed at by this invention. They consequently found that some of the hydantoin compound derivatives are capable of enhancing the recording sensitivity highly satisfactorily without entailing any impairment of the whiteness of the recording layer.

Specifically, this invention relates to an additive consisting essentially of a hydantoin compound represented by the following formula [I]:

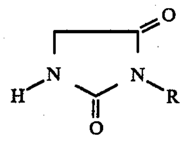

[I]

(wherein R stands for an alkyl group of 8 to 20 carbon atoms) for a heat-sensitive recording material, a heat-sensitive recording material containing the additive, and a method for the production of the recording material.

DETAILED DESCRIPTION OF THE PREFERRED EMBODIMENTS

The mechanism by which the hydantoin compound in the additive of this invention enhances the recording sensitivity without sacrifice of the whiteness of the recording layer is still unknown. One possibility is that the compound represented by the formula [I] helps to enhance the compatibility among the components of the mixed system (sensitive layer) during the fusion thereof.

From the viewpoint that the whiteness of the sensitive layer should not be impaired by the additive, the substituent R at the 3 position in the formula [I] of the hydantoin compound is limited to an alkyl group of no less than 8 carbon atoms. From the viewpoint of the ease of procurement of raw material, the substituent R at the 3 position of the formula [I] of the hydantoin compound is limited to an alkyl group of no more than 20 carbon atoms.

Of the hydantoin compounds represented by the formula [I], those which have a 2-ethylhexyl group of 8 carbon atoms, an n-tetradecyl group of 14 carbon atoms, an n-hexadecyl group of 16 carbon atoms, an n-octadecyl group of 18 carbon atoms, and an n-eicosyl group of 20 carbon atoms respectively as the substituent R are novel. The compounds of the formula [I] including the novel compounds mentioned above can be easily produced in high yields by any of the conventional methods such as, for example, the method reported in Encycl. Chem. Tech., 2nd ed. vol. 11, page 142, namely by causing hydantoin to be reacted upon by an alkyl halide in combination with an alkali such as sodium hydroxide, potassium hydroxide, sodium carbonate, or potassium carbonate in a polar aprotic solvent.

This method of production will be described more specifically below. The polar aprotic solvents usable for the reaction include dimethyl sulfoxide (DMSO), dimethyl formamide (DMF), diethyl formamide, dimethyl acetamide, acetonitrile, sulforan, dimethyl sulforan, acetone, and nitrobenzene, for example. Though this solvent tolerates the presence of a small amount of water or some other organic solvent, it is required to exhibit stability under the reaction conditions.

The reaction of hydantoin with the alkyl halide is carried out in the polar aprotic solvent in the presence of an alkali, using the hydantoin, alkyl halide, and alkali in equivalent. The molar ratio of these reactants may be varied when necessary.

The use of hydantoin or the alkyl halide in an excess amount is uneconomical and also entails the disadvantage that the reaction gives rise to a secondary product and thus requires extra time and labor for the separation of the secondary product and raw materials from the resultant product. Thus, excess use of any of the reactants should be avoided. Generally, the molar ratio of the alkyl halide to the hydantoin is approximately in the range of 1:0.5 to 1:3.0 and the concentrations of these reactants in the polar aprotic solvent are each desired to be approximately in the range of 5 to 80% by weight. The alkali is desired to be used in at least an equivalent relative to the hydantoin or the alkyl halide.

The alkyl halide for the reaction is suitably used in the form of a chloride, a bromide, or an iodide.

The reaction is generally carried out at a temperature in the range of 50° to 200° C., preferably 80° to 160° C. Though this reaction is ordinarily carried out under normal pressure, it may be conducted under application of pressure when necessary. A reaction time in the range of around 5 minutes to four hours is sufficient.

The 3-N-alkyl hydantoin which is produced by this invention can be isolated from the reaction solution by a conventional treatment. For example, there can be used a procedure which comprises filtering the reaction solution thereby separating the by-produced alkali metal salt from the resultant product and then distilling the filtrate thereby expelling the solvent and obtaining crude crystals. The purified 3-N-alkyl hydantoin is obtained by recrystallizing the crude crystals with a solvent such as alcohol. The recrystallization may be carried out, when necessary, in the presence of a refining agent such as activated carbon.

The hydantoin compounds obtained by the reaction described above for use as the additive for the heat-sensitive recording material include 3-N-octyl hydantoin, 3-N-decyl hydantoin, 3-N-dodecyl hydantoin, 3-N-tetradecyl hydantoin, 3-N-hexadecyl hydantoin, 3-N-octadecyl hydantoin, 3-N-eicosyl hydantoin, and 3-N-(2-ethylhexyl)-hydantoin, for example.

For the additive of this invention, these hydantoins may be used either singly or in the form of a mixture of two or more members. The additive is allowed to incorporate further therein, though to an extent such that the effect aimed at by the present invention is not impaired, fatty acid amides such as stearic acid amide, stearic acid methylene bisamide, oleic acid amide, palmitic acid amide, and coconut fatty acid amide, hindered phenols such as 2,2′-methylenebis(4-methyl-6-t-butyl phenol), 4,4′-butylidenebis(6-t-butyl-3-methyl phenol), and 1,1′,3-tris(2-methyl-4-hydroxy-5-t-butyl phenol)butane, ultraviolet light absorbents such as 2-(2′-hydroxy-5′-methyl phenyl)-benzotriazole, and 2-hydroxy-4-benzyloxy benzophenone and any of various well-known heat-fusible substances.

The amount of the additive of the specific construction described above to be used for the purpose of this invention is not absolutely defined but is generally in the range of 0.1 to 10 parts by weight, preferably 1.0 to 5.0 parts by weight, based on 1 part by weight of the developer.

Now, the heat-sensitive recording material of this invention which uses the additive of this invention will be described below.

The following compounds may be cited as concrete examples of the colorless or slightly colored basic dye to be used for the formation of the recording layer in the heat-sensitive recording material.

Triaryl methane type dyes such as 3,3-bis(p-dimethylaminophenyl)-6-dimethylaminophthalide, 3,3-bis-(p-dimethylaminophenyl)phthalide, 3-(p-dimethylaminophenyl)-3-(1,2-dimethylindol-3-yl)phthalide, 3-(p-dimethylaminophenyl)-3-(2-methylindol-3-yl)phthalide, 3,3-bis(1,2-dimethylindol-3-yl)-5-dimethylaminophthalide, 3,3-bis(1,2-dimethylindol-3-yl)-6-dimethylaminophthalide, 3,3-bis(9-ethylcarbazol-3-yl)-6-dimethylaminophthalide, 3,3-bis(2-phenylindol-3-yl)-6-dimethylaminophthalide, and 3-p-dimethylaminophenyl-3-(1-methylpyrrol-3-yl)-6-dimethylaminophthalide; diphenyl methane type dyes such as 4,4′-bis-dimethylaminobenzhydryl benzyl ether, N-halophenylleucoauramines, and N-2,4,5-trichlorophenyl leucoauramine; thiazine type dyes such as benzoyl leucomethylene blue and p-nitrobenzoyl leucomethylene blue; spiro type dyes such as 3-methyl-spirodinaphthopyrane, 3-ethyl-spirodinaphthopyran 3-phenyl-spiro-dinaphthopyran, 3-benzyl-spiro-dinaphthopyran, 3-methyl-naphtho(6′-methoxybenzo)spiropyran, 3,3′-dichloro-spiro-dinaphthopyran, and 3-propyl-spiro-dibenzopyran; lactam type dyes such as rhodamine-B-anilinolactam, rhodamine(p-nitroanilino)lactam, rhodamine(o-chloroanilino)lactam, and rhodamine B(p-chloroanilino)-lactam; and 3-dimethylamino-7-methoxyfluoran, 3-diethylamino-6-methoxyfluoran, 3-diethylamino-7-methoxyfluoran, 3-diethylamino-7-chlorofluoran, 3-diethylamino-6-methyl-7-chlorofluoran, 3-diethylamino-6,7-dimethylfluoran, 3-(N-ethyl-p-toluidino)-7-methylfluoran, 3-diethylamino-7-N-acetyl-N-methylaminofluoran, 3-diethylamino-7-N-methylaminofluoran, 3-diethylamino-7-dibenzylaminofluoran, 3-diethylamino-7-N-methyl-N-benzylaminofluoran, 3-diethylamino-7-N-chloroethyl-N-methylaminofluoran, 3-diethylamino-7-N-diethylaminofluoran, 3-(N-ethyl-p-toluidino)-6-methyl-7-phenylaminofluoran, 3-(N-ethyl-p-toluidino)-6-methyl-7-(p-toluidinofluoran, 3-diethylamino-6-methyl-7-phenylaminofluoran, 3-dibutylamino-6-methyl-7-phenylaminofluoran, 3-diethylamino-7-(2-carbomethoxyphenylamino)fluoran, 3-(n-cyclohexyl-N-methylamino)-6-methyl-7-phenylaminofluoran, 3-pyrrolidino-6-methyl-7-phenylaminofluoran, 3-piperidino-6-methyl-7-phenylaminofluoran, 3-diethylamino-6-methyl-7-xylidinofluoran, 3-diethylamino-7-(o-chlorophenylamino)fluoran, 3-dibutylamino-7-(o-chlorophenylamino)fluoran, 3-pyrrolidino-6-methyl-7-p-butylphenylaminofluoran, 3-(N-methyl-N-n-amyl-)amino-6-methyl-7-phenylaminofluoran, 3-(N-ethyl-N-n-amyl)amino-6-methyl-7-phenylaminofluoran, 3-(N-ethyl-N-isoamyl)amino-6-methyl-7-phenylaminofluoran, 3-(N-methyl-N-n-hexyl)amino-6-methyl-7-phenylaminofluoran, 3-(N-ethyl-N-n-hexyl)amino-6-methyl-7-phenylaminofluoran, 3-(N-ethyl-N-β-ethylhexyl)amino-6-methyl-7-phenylaminofluoran, 3-(N-methyl-N-tetrahydrofurfurylamino)-6-methyl-7-phenylaminofluoran, 3-(N-ethyl-N-tetrahydrofurfurylamino)-6-methyl-7-phenylaminofluoran, 2,2-bis[4-{6′-(N-cyclohexyl-N-methylamino)-3′-methylspiro[phthalide-3,9′-xanthen]-2′-ylamino}phenyl]propane, and 2,2-bis[4-{6′-(N-cyclohexyl-N-methylamino)-3′-methylspiro(phthalide-3,9′-xanthene)-2′-ylamino}phenyl]butane.

The developer to be used in combination with the basic dye mentioned above is not specifically defined. The developer is required to be liquefied, gasified, or dissolved at elevated temperatures and to cause the basic dye to assume a color on contact therewith. As typical concrete examples of the developer fulfilling this requirement, there may be cited phenolic compounds such as 4-tert-butyl phenol, α-naphthol, β-naphthol, 4-acetylphenol, 4-tert-octylphenol, 4,4'-sec-butylidenediphenol, 4-phenylphenol, 4,4'-dihydroxy-diphenyl methane, 2,2-bis(4-hydroxyphenyl) propane, 4-hydroxyacetophenol, 4-tert-octyl catechol, 2,2'-dihydroxydiphenol, 2,2'-methylenebis(4-methyl-6-tert-isobutylpheol), 4,4'-isopropylidenebis(2-tert-butylphenol), 2,2'-methylenebis(4-chlorophenol), 2,2-bis(3-methyl-4-hydroxy)propane, 1,1-bis(4-hydroxyphenyl)ethane, 2,2-bis(4-hydroxyphenyl)-4-methylpentane, 4,4'-benzylidenebisphenol, hydroquinone, 4,4'-cyclohexylidenediphenol, 4,4'-dihydroxydiphenylsulfide, 4,4'-thiobis(6-tert-butyl-3-methylphenol), 3,4-dihydroxydiphenyl-p-tolylsulfone, 4-hydroxy-4'-chlorodipheylsulfone, 4-hydroxy-4'-isopropoxydiphenylsulfone, bis(3-allyl-4-hydroxyphenyl)-sulfone, 3-chloro-4-hydroxydiphenylsulfone, 4,4'-dihydroxydiphenylsulfone, hydroquinone monobenzyl ether, 4-hydroxybenzophenone, 2,4-dihydroxybenzophenone, 2,4,4'-trihydroxybenzophenone, 2,2',4,4'-tetrahydroxybenzophenone, dimethyl 4-hydroxyphthalate, methyl 4-hydroxybenzoate, ethyl 4-hydroxybenzoate, propyl 4-hydroxybenzoate, sec-butyl 4-hydroxybenzoate, pentyl 4-hydroxybenzoate, phenyl 4-hydroxybenzoate, benzyl 4-hydroxybenzoate, tolyl 4-hydroxybenzoate, chlorophenyl 4-hydroxybenzoate, phenylpropyl 4-hydroxybenzoate, phenetyl 4-hydroxybenzoate, p-chlorobenzyl 4-hydroxybenzoate, p-methoxybenzyl 4-hydroxybezoate, pentamethylenebis-4-hydroxybenzoic acid, propyl gallate, lauryl gallate, and stearyl gallate; aromatic carboxylic acids such as benzoic acid, p-tert-butylbenzoic acid, trichlorobenzoic acid, terephthalic acid, 3-sec-butyl-4-hydroxybenzoic acid, 3-cyclohexyl-4-hydroxybenzoic acid, 3,5-dimethyl-4-hydroxybezoic acid, salicylic acid, 3-isopropylsalicylic acid, 3-tert-butylsalicylic acid, 3-benzylsalicylic acid, 3-(α-methylbenzyl)salicylic acid, 3-chloro-5-(α-methylbenzyl)salicylic acid, 3,5-di-tert-butylsalicylic acid, 3-phenyl-5-(α,α-dimethylbenzyl)salicylic acid, 3,5-di-α-methylbenzyl salicylic acid; salts of such phenolic compounds and aromatic carboxylic acids as mentioned above with such polyvalent metals as zinc, magnesium, aluminum, calcium, titanium, manganese, tin, and nickel.

The ratio of the amounts of the basic dye and the developer to be used is generally such that the proportion of the developer is approximately in the range of 1.0 to 5.0 parts by weight, preferably 1.5 to 3.0 parts by weight, based on 1 part by weight of the dye. Of course, the basic dye and the developer may each be used in the form of a mixture of two or more members.

Besides the basic dye and the developer, the heat-sensitive recording material may incorporate an inorganic pigment. As examples of the inorganic pigment, there may be cited calcium carbonate, aluminum hydroxide, talc, kaoline, diatomaceous earth, titanium dioxide, magnesium carbonate, and silicon oxide. Further, the heat-sensitive recording material may incorporate therein a dispersion of such a salt as zinc stearate or calcium stearate for the purpose of keeping the recording layer from sticking on contact with the recording head.

Further, for the purpose of acquiring improved adhesiveness to a substrate such as paper, the heat-sensitive recording material may incorporate therein as a binder 2 to 40% by weight, preferably 5 to 25% by weight, based on the total weight of solids, of starch hydroxy cellulose, carboxymethyl cellulose, gelatine, casein, polyvinyl alcohol, or styrene-maleic anhydride copolymer where water is used as a dispersant, or 10 to 50% by weight, preferably 20 to 40% by weight, based on the total weight of solids, of methyl methacrylate resin, for example, when an organic solvent such as toluene or methylethyl ketone is used as a dispersant. The substances useful as a binder herein are of course not limited to those mentioned above.

For the production of the heat-sensitive recording material by the use of various components for the heatgraphic coloring layer, any of the well-known methods may be employed. For example, this production can be accomplished by adding the aforementioned basic dye, developer, heat-fusible substance, inorganic pigment, and other additives independently of one another in combination with the binder or adding the basic dye and the mixture of the other components separately of each other in combination with an aqueous polyvinyl alcohol solution to an aqueous medium, grinding and dispersing the resultant separate blends in a dispersing device such as a ball mill or an attriter thereby preparing dispersed liquids each in the form of a coating liquid, then blending the dispersed liquids thereby preparing a heat-sensitive coloring layer, and then applying the layer on a substrate such as paper and drying the applied layer, as commonly practiced heretofore.

The amount of the heat-sensitive coloring layer to be applied on the paper or other substrate is not specifically defined. Generally this amount is in the range of 2 to 12 $g/m^2$, preferably 3 to 10 $g/m^2$, on dry basis.

The material of this substrate is not specifically defined. Paper, synthetic fiber paper, film of synthetic resin, or other similar material may be suitably used.

Further, an overcoat layer may be superposed on the recording layer for the purpose of protecting the recording layer. It is of course permissible to form an undercoat layer on the substrate prior to the application of the heat-sensitive coloring layer thereon. The recording layer may be given any of the treatments heretofore known to the art.

The heat-sensitive recording material obtained by using the additive of this invention as described above is well rounded in its qualities as it possesses excellent high recording speed while suffering only minimal loss of whiteness.

Now, the synthesis of a hydantoin compound as an additive of this invention for a heat-sensitive recording material, the heat-sensitive recording material using the hydantoin compound, and the method for the production of the recording material will be described specifically below with reference to working examples. These examples are cited exclusively for facilitating an understanding of the present invention. This invention is of course not limited to these examples and it is not restricted in any sense by the examples.

Synthesis 1 Synthesis of 3-N-tetradecyl hydantoin

A separable flask having an inner volume of 1 liter and provided with a thermometer, a reflux condenser, and a stirrer were set in a constant temperature bath.

In this flask, 400 ml of DMF, 50.0 g (0.50 mol) of hydantoin, 116.4 g (0.50 mol) of tetradecyl chloride, and 34.6 g of potassium carbonate (0.25 mol) were placed and refluxed for one hour for reaction.

The resultant reaction solution was filtered to remove by-produced salts, distilled under a vacuum to expel the solvent, and dried to obtain crude crystals. The crude crystals and 450 ml of methanol added thereto were refluxed to dissolve the crude crystals. The resultant solution, in the presence of 10.0 g of activated carbon, was refluxed for 30 minutes. The refluxed solution was filtered to remove the activated carbon under heating. The filtrate was cooled to 10° C. and centrifuged to recover 124.0 g (yield 84%) of crystals of 3-N-tetradecyl hydantoin.

Synthesis 2 - Synthesis of 3-N-hexadecyl hydantoin

The procedure of Synthesis 1 was repeated, except that 130.5 g (0.50 mol) of hexadecyl chloride was used in place of 116.4 g of tetradecyl chloride and 450 ml of chloroform was used in place of 450 ml of methanol. Consequently, there was obtained 131.4 g (yield 81%) of 3-N-hexadecyl hydantoin.

Synthesis 3 Synthesis of 3-N-octadecyl hydantoin

The procedure of Synthesis 2 was repeated, except that 144.5 (0.50 mol) of octadecyl chloride was used in place of hexadecyl chloride. Consequently, there was obtained 150.0 g (yield 85%) of 3-N-octadecyl hydantoin.

Syntheses 4 to 8

By the same procedure, compounds having 2-ethylhexyl, n-octyl, n-decyl, n-dodecyl, and n-eicosyl respectively as an alkyl at the 3 position were synthesized. These compounds and the compounds obtained in Syntheses 1 to 3 were identified by mass spectrometry, elementary analysis, IR spectrometry, and NMR spectrometry.

The results of these measurements are shown in the Table 1.

TABLE 1

| Alkyl group at 3 position | Mass spectrum ($M^+$) | Elementary analysis | C | H | N | O | IR absorption water length ($cm^{-1}$) | H-NMR (ppm) |
|---|---|---|---|---|---|---|---|---|
| 2-ethylhexyl | 212 | (Found) | 62.51 | 9.41 | 12.89 | 15.19 | 3230, 2920, 2860, | 0.9(6H, tx2), 1.3(9H, m), |
| | | (Calculated) | 62.23 | 9.50 | 13.20 | 15.07 | 1770, 1690, 1460, | 3.4(2H, w), 4.0(2H, s), |
| | | | | | | | 1420, 720 | 6.5(1H, s) |
| n-octyl | 212 | (Found) | 61.57 | 9.73 | 13.82 | 14.88 | same as above | 0.9(3H, t), 1.3(12H, m), |
| | | (Calculated) | 62.23 | 9.50 | 13.20 | 15.07 | | 3.5(2H, t), 4.0(2H, s), |
| | | | | | | | | 6.5(1H, s) |
| n-decyl | 240 | (Found) | 64.64 | 10.21 | 11.88 | 13.27 | same as above | 0.9(3H, t), 1.3(16H, m), |
| | | (Calculated) | 64.96 | 10.07 | 11.66 | 13.31 | | 3.5(2H, t), 4.0(2H, s), |
| | | | | | | | | 6.5(1H, s) |
| n-dodecyl | 268 | (Found) | 67.42 | 10.78 | 10.22 | 11.58 | same as above | 0.9(3H, t), 1.3(20H, m), |
| | | (Calculated) | 67.12 | 10.52 | 10.44 | 11.92 | | 3.5(2H, t), 4.0(2H, s), |
| | | | | | | | | 6.4(1H, s) |
| n-tetradecyl | 296 | (Found) | 69.16 | 10.53 | 9.21 | 11.10 | same as above | 0.9(3H, t), 1.3(24H, m), |
| | | (Calculated) | 68.88 | 10.88 | 9.45 | 10.79 | | 3.5(2H, t), 4.0(2H, s) |
| | | | | | | | | 6.3(1H, s) |
| n-hexadecyl | 324 | (Found) | 70.01 | 11.37 | 8.76 | 9.86 | same as above | 0.9(3H, t), 1.3(28H, m), |
| | | (Calculated) | 70.33 | 11.18 | 8.63 | 9.86 | | 3.5(2H, t), 4.0(2H, s), |
| | | | | | | | | 6.3(1H, s) |
| n-octadecyl | 352 | (Found) | 71.91 | 11.33 | 7.78 | 8.98 | same as above | 0.9(3H, t), 1.3(32H, m), |
| | | (Calculated) | 71.53 | 11.44 | 7.95 | 9.08 | | 3.5(2H, t), 4.0(2H, s), |
| | | | | | | | | 6.3 (1H, s) |
| n-eicocyl | 380 | (Found) | 72.19 | 11.79 | 7.44 | 8.58 | same as above | 0.9(3H, t), 1.3(36H, m), |
| | | (Calculated) | 72.58 | 11.65 | 7.36 | 8.41 | | 3.5(2H, t), 4.0(2H, s), |
| | | | | | | | | 6.3(1H, s) |

EXAMPLE 1

| | |
|---|---|
| (Dispersed liquid A) | |
| 2,2-Bis[4-{6'-(N-cyclohexyl-N-methylamino)-3'-methylspiro[phthalide-3,9'-xanthene]-2'-ylamino}-phenyl]propane | 25 parts by weight |
| Aqueous 15% polyvinyl alcohol solution | 25 parts by weight |
| Water | 50 parts by weight |

-continued

| | |
|---|---|
| (Dispersed liquid B) | |
| 3,4-Dihydroxyphenyl-p-tolylsulfone | 25 parts by weight |
| Aqueous 15% polyvinyl alcohol solution | 25 parts by weight |
| Water | 50 parts by weight |
| (Dispersed liquid C) | |
| 3-N-dodecyl hydantoin | 25 parts by weight |
| Aqueous 15% polyvinyl alcohol solution | 25 parts by weight |
| Water | 50 parts by weight |

The compositions mentioned above were separately ground and dispersed in a paint conditioner for 24 hours to obtain dispersed liquids A, B and C.

Then, a coating liquid was produced by stirring 10 parts by weight of the liquid (A), 25 parts by weight of the liquid (B), 30 parts by weight of the liquid (C), 30 parts by weight of an aqueous 50% calcium carbonate dispersion, and 5 parts by weight of an aqueous 15% polyvinyl alcohol solution. A heat-sensitive recording paper was produced by applying the coating liquid with a wire bar on plain paper 50 g/$m^2$ in basis weight in an amount calculated to produce a dry layer at a coating rate of 10 g/$m^2$ and drying the applied layer.

EXAMPLE 2

| | |
|---|---|
| (Dispersed liquid D) | |
| 2,2-Bis(4-hydroxyphenyl)propane | 25 parts by weight |
| Aqueous 15% polyvinyl alcohol solution | 25 parts by weight |
| Water | 50 parts by weight |
| (Dispersed liquid E) | |
| 3-N-hexadecyl hydantoin | 25 parts by weight |
| Aqueous 15% polyvinyl alcohol solution | 25 parts by weight |
| Water | 50 parts by weight |

The dispersed liquids (D) and (E) were prepared in the same manner as in Example 1. A heat-sensitive recording paper was produced by following the procedure of Example 1, except that 10 parts by weight of the liquid (A), 25 parts by weight of the liquid (D), and 30 parts by weight of the liquid (E) were used instead.

EXAMPLE 3

| | |
|---|---|
| (Dispersed liquid F) | |
| 3-(N-cyclohexyl-N-methylamino)-6-methyl-7-phenylaminofluoran | 25 parts by weight |
| Aqueous 15% polyvinyl alcohol solution | 25 parts by weight |
| Water | 50 parts by weight |
| (Dispersed liquid G) | |
| 3-N-octadecyl hydantoin | 25 parts by weight |
| Aqueous 15% polyvinyl alcohol solution | 25 parts by weight |
| Water | 50 parts by weight |

The dispersed liquids (F) and (G) were prepared in the same manner as in Example 1. A heat-sensitive recording paper was produced by following the procedure of Example 1, except that 10 parts by weight of the liquid (F), 25 parts by weight of the liquid (D), and 30 parts by weight of the liquid (G) were used instead.

EXAMPLE 4

| | |
|---|---|
| (Dispersed liquid H) | |
| 3-N-eicosyl hydantoin | 25 parts by weight |
| Aqueous 15% polyvinyl alcohol solution | 25 parts by weight |
| Water | 50 parts by weight |

The dispersed liquid (H) was prepared in the same manner as in Example 1. A heat-sensitive recording paper was produced by following the procedure of Example 1, except that 10 parts by weight of the liquid (A), 25 parts by weight of the liquid (D), and 30 parts by weight of the liquid (H) were used instead.

EXAMPLE 5

| | |
|---|---|
| (Dispersed liquid I) | |
| 3-N-(2-ethylhexyl)hydantoin | 25 parts by weight |
| Aqueous 15% polyvinyl alcohol solution | 25 parts by weight |
| Water | 50 parts by weight |

The dispersed liquid (I) was prepared in the same manner as in Example 1. A heat-sensitive recording paper was produced by following the procedure of Example 1, except that 10 parts by weight of the liquid (A), 25 parts by weight of the liquid (D), and 30 parts by weight of the liquid (I) were used instead.

EXAMPLE 6

| | |
|---|---|
| (Dispersed liquid J) | |
| 3-N-tetradecyl hydantoin | 25 parts by weight |
| Aqueous 15% polyvinyl alcohol solution | 25 parts by weight |
| Water | 50 parts by weight |

The dispersed liquid (J) was prepared in the same manner as in Example 1. A heat-sensitive recording paper was produced by following the procedure of Example 1, except that 10 parts by weight of the liquid (A), 25 parts by weight of the liquid (D), and 30 parts by weight of the liquid (J) were used instead.

EXAMPLE 7

| | |
|---|---|
| (Dispersed liquid K) | |
| 3-N-octyl hydantoin | 25 parts by weight |
| Aqueous 15% polyvinyl alcohol solution | 50 parts by weight |
| Water | 50 parts by weight |

-continued

The dispersed liquid (K) was prepared in the same manner as in Example 1. A heat-sensitive recording paper was produced by following the procedure of Example 1, except that 10 parts by weight of the liquid (F), 25 parts by weight of the liquid (D), and 30 parts by weight of the liquid (K) were used instead.

EXAMPLE 8

| | |
|---|---|
| (Dispersed liquid L) | |
| 3-N-decyl hydantoin | 25 parts by weight |
| Aqueous 15% polyvinyl alcohol solution | 50 parts by weight |
| Water | 50 parts by weight |

The dispersed liquid (L) was prepared in the same as in Example 1. A heat-sensitive recording paper was produced by following the procedure of Example 1, except that 10 parts by weight of the liquid (F), 25 parts by weight of the liquid (D), and 30 parts by weight of the liquid (L) were used instead.

COMPARATIVE EXPERIMENT 1

A heat-sensitive recording paper was produced by following the procedure of Example 1, except that diphenyl carbonate was used in place of 3-N-dodecyl hydantoin in the dispersed liquid (C).

COMPARATIVE EXPERIMENT 2

A heat-sensitive recording paper was produced by following the procedure of Example 2, except that stearic acid amide was used in place of 3-N-hexadecyl hydantoin in the dispersed liquid (E).

COMPARATIVE EXPERIMENT 3

A heat-sensitive recording paper was produced by following the procedure of Example 3, except that phenyl 1-hydroxy-2-naphthoate was used in place of 3-N-octadecyl hydantoin in the dispersed liquid (G).

COMPARATIVE EXPERIMENT 4

A heat-sensitive recording paper was produced by following the procedure of Example 6, except that 3-N-hexyl hydantoin was used in place of 3-N-tetradecyl hydantoin in the dispersed liquid (J).

The 12 heat-sensitive recording materials produced as described above were treated at 110° C. under a pressure of 1 kg/cm$^2$ for 0.2 second. The images developed in black were tested with a Macbeth densitometer and were tested for whiteness with a Hunter multipurpose reflectometer.

For determination of thermal stability, 12 samples were left standing at 60° C. for 24 hours and then tested for whiteness with a Hunter multipurpose relfectometer.

The results are shown in the following Table 2.

TABLE 2

| | Density of developed color | Whiteness | Thermal Stability |
|---|---|---|---|
| Example 1 | 1.29 | 84.7 | 80.5 |
| Example 2 | 1.23 | 84.2 | 80.7 |
| Example 3 | 1.20 | 85.1 | 82.6 |
| Example 4 | 1.23 | 84.4 | 81.8 |
| Example 5 | 1.16 | 85.0 | 80.3 |
| Example 6 | 1.28 | 85.2 | 82.0 |

TABLE 2-continued

| | Density of developed color | Whiteness | Thermal Stability |
|---|---|---|---|
| Example 7 | 1.31 | 83.8 | 78.9 |
| Example 8 | 1.30 | 84.1 | 80.1 |
| Comparative Experiment 1 | 1.30 | 84.9 | 65.1 |
| Comparative Experiment 2 | 1.00 | 84.9 | 81.7 |
| Comparative Experiment 3 | 1.10 | 85.2 | 82.2 |
| Comparative Experiment 4 | 1.32 | 84.5 | 50.9 |

It is noted clearly from the preceding table that the products of Examples 1 to 8 excelled in balance between density of developed color and thermal stability as compared with those of Comparative Experiments 1 to 4.

What is claimed is:

1. A hydantoin compound represented by the following formula:

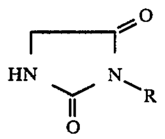

wherein R is one member selected from the group consisting of 2-ethylhexyl, n-tetradecyl, n-hexadecyl, n-octadecyl and n-eicosyl.

* * * * *